United States Patent
Katzlinger et al.

(10) Patent No.: US 10,222,254 B2
(45) Date of Patent: Mar. 5, 2019

(54) SYSTEM FOR OPTICALLY MONITORING OPERATING CONDITIONS IN A SAMPLE ANALYZING APPARATUS

(71) Applicant: Molecular Devices (Austria) GmbH, Wals (AT)

(72) Inventors: Michael Katzlinger, Eugendorf (AT); Georg Kronberger, Salzburg (AT); Bernhard Schinwald, Mundafing (AT)

(73) Assignee: Molecular Devices (Austria) GmbH, Wals (AT)

( * ) Notice: Subject to any disclaimer, the term of this patent is extended or adjusted under 35 U.S.C. 154(b) by 0 days.

(21) Appl. No.: 15/344,680

(22) Filed: Nov. 7, 2016

(65) Prior Publication Data
US 2018/0128676 A1    May 10, 2018

(51) Int. Cl.
*G01J 1/02* (2006.01)
*G01N 21/64* (2006.01)
*G01N 35/10* (2006.01)
*G01N 35/00* (2006.01)
*G01N 35/04* (2006.01)

(52) U.S. Cl.
CPC .......... *G01J 1/0228* (2013.01); *G01J 1/0219* (2013.01); *G01J 1/0238* (2013.01); *G01N 21/6452* (2013.01); *G01N 21/6458* (2013.01); *G01N 35/00623* (2013.01); *G01N 2021/6482* (2013.01); *G01N 2035/00643* (2013.01); *G01N 2035/00752* (2013.01); *G01N 2035/00801* (2013.01); *G01N 2035/0418* (2013.01); *G01N 2035/0494* (2013.01); *G01N 2035/1013* (2013.01); *G01N 2035/1018* (2013.01); *G01N 2201/0238* (2013.01)

(58) Field of Classification Search
CPC ...... G01J 1/0219; G01J 1/0228; G01J 1/0238; G01J 21/6452; G01J 21/6458; G01J 2021/6482; G01J 2201/0238
See application file for complete search history.

(56) References Cited

U.S. PATENT DOCUMENTS

| | | | |
|---|---|---|---|
| 6,099,230 A | 8/2000 | Hitch | |
| 8,101,426 B2 * | 1/2012 | Durack | ............ G01N 15/1459 422/50 |
| 2015/0064740 A1 | 3/2015 | Nagai et al. | |

FOREIGN PATENT DOCUMENTS

| AU | 2008229929 A1 | 11/2008 |
|---|---|---|
| WO | 2006102414 A2 | 9/2006 |

OTHER PUBLICATIONS

International Search Report and Written Opinion for PCT/IB2017/056889 dated Feb. 19, 2018.

* cited by examiner

*Primary Examiner* — Mark R Gaworecki

(57) ABSTRACT

A sample analyzing apparatus for performing an optical-based measurement on a sample includes a housing, a first light source, excitation optics, a first light detector, emission optics, and a monitoring system, all of which are disposed in the housing. The monitoring system is configured for monitoring a movable component disposed in the housing. The monitoring system includes one or more light sources for illuminating the movable component, and one or more light detectors for detecting light reflected from the movable component in response to being illuminated.

21 Claims, 4 Drawing Sheets

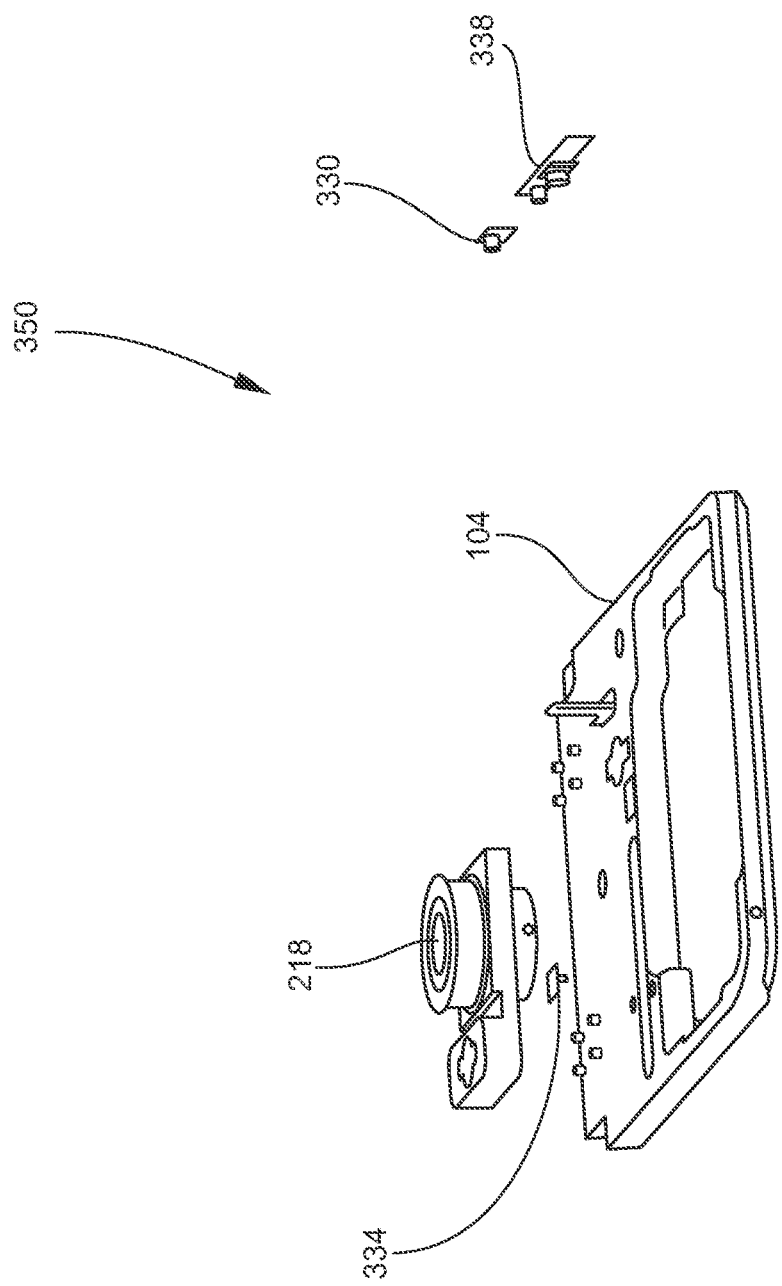

SYSTEM FOR OPTICALLY MONITORING OPERATING CONDITIONS IN A SAMPLE ANALYZING APPARATUS

TECHNICAL FIELD

The present invention generally relates to systems, apparatuses, and methods for optical-based monitoring of various operating conditions internal to a sample analyzing apparatus. The sample analyzing apparatus may be one that carries out one or more types of optical-based measurements or analyses of samples, such as fluorescence-based, absorbance-based, and/or luminescence-based measurements, and/or microscopic imaging.

BACKGROUND

Various analytical instruments have been developed for making optics-based measurements (e.g., fluorescence, luminescence, absorbance, microscopy, etc.) on samples (e.g., chemical compounds, biological material, etc.) as part of assays useful in the life science industry. Many analytical instruments are designed to carry out only one or a few dedicated types of measurements. On the other hand, multimode analytical instruments, also referred to as multimode readers, are designed to perform multiple analytical assays in a single instrument. Multimode analytical instruments may be designed to be re-configurable to enable a user to select different types of measurements to be performed. Some multimode analytical instruments utilize application-specific cartridges to enable re-configuration. The samples analyzed or measured by an analytical instrument typically supported in a multi-well microtiter plate (also known as microplate or optical plate), although other types of sample holders or containers may be utilized. The microplate containing the samples is typically loaded into the interior of the analytical instrument, and the interior is isolated from the ambient to enable optical-based measurement or imaging to be performed.

Depending on the type(s) of analysis an analytical instrument is capable of performing on a sample, the analytical instrument may include various types of movable components, such as fluidic components (e.g., nozzles, pipettes, etc.), optical components (e.g., lenses, etc.), and mechanical components (e.g., motorized stages, microtiter plate transports, etc.) that operate in the closed interior of the analytical instrument. It would be desirable to be able to monitor these movable components, including determining the presence and position of such components.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to an embodiment, a sample analyzing apparatus for performing an optical-based measurement on a sample includes: a housing; a first light source disposed in the housing and configured for generating excitation light; excitation optics disposed in the housing and configured for directing the excitation light from the first light source to the sample, wherein the sample emits emission light in response to being irradiated by the excitation light; a first light detector disposed in the housing and configured for measuring the emission light; emission optics disposed in the housing and configured for directing the emission light from the sample to the first light detector; and a monitoring system configured for monitoring a movable component disposed in the housing, the monitoring system including: a second light source disposed in the housing and configured for illuminating the movable component; and a second light detector disposed in the housing and configured for detecting light reflected from the movable component in response to being illuminated.

According to another embodiment, a method is provided for monitoring a movable component of a sample analyzing apparatus. The sample analyzing apparatus includes a housing in which the movable component is disposed, a first light source disposed in the housing and configured for generating excitation light, excitation optics disposed in the housing and configured for directing the excitation light from the first light source to a sample disposed in the housing, a first light detector disposed in the housing and configured for measuring emission light emitted from the sample in response to being irradiated by the excitation light, and emission optics disposed in the housing and configured for directing the emission light from the sample to the first light detector. The method includes: operating a monitoring system to monitor the movable component by: operating a second light source disposed in the housing to illuminate the movable component; and operating a second light detector disposed in the housing detect light reflected from the movable component in response to being illuminated.

Other devices, apparatuses, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 4 is a perspective view of a monitoring system that may be included with a sample analyzing apparatus such as illustrated in FIGS. 1 and 2, according to an embodiment.

DETAILED DESCRIPTION

As used herein, the term "analyte" generally refers to a substance to be detected or measured by an optical-based technique. Examples of analytes include, but are not limited to, proteins (including membrane-bound proteins), antigenic substances, haptens, antibodies, toxins, organic compounds, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the foregoing (as applicable), and combinations of two or more of any of the foregoing.

As used herein, the term "sample" generally refers to a material known or suspected of containing the analyte. In implementing the subject matter disclosed herein, the sample may be utilized directly as obtained from the source or following a pretreatment to modify the character of the sample. The sample may be derived from any biological source, such as a physiological fluid, including for example blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The sample may be pretreated prior to use, such as preparing plasma from blood, diluting viscous fluids, and the like. Methods of pretreatment can involve filtration, precipitation, dilution, distillation, concentration, inactivation of interfering components, chromatography, separation steps, and the addition of reagents. Besides physiological fluids, other liquid samples may be used such as water, food products and the like for the performance of environmental or food production assays. In addition, a solid material known or suspected of containing the analyte may be used as the sample. In some instances it may be beneficial to modify a solid sample to form a liquid medium or to release the analyte from the solid sample.

As used herein, the term "light" generally refers to electromagnetic radiation, quantizable as photons. As it pertains to the present disclosure, light may propagate at wavelengths ranging from ultraviolet (UV) to infrared (IR). In the present disclosure, the term "light" is not intended to be limited to electromagnetic radiation in the visible range. In the present disclosure, the terms "light," "photons," and "radiation" are used interchangeably.

As used herein, in relation to the detection or measurement of optical signals emanating from a sample, terms such as "emission light" or "emitted light" refer to light emitted from the sample as a consequence of fluorescence or luminescence. Additionally, for convenience terms such as "emission light" or "emitted light" also refer to light that is transmitted through a sample and collected for the purpose of measuring absorbance.

Figure 1:
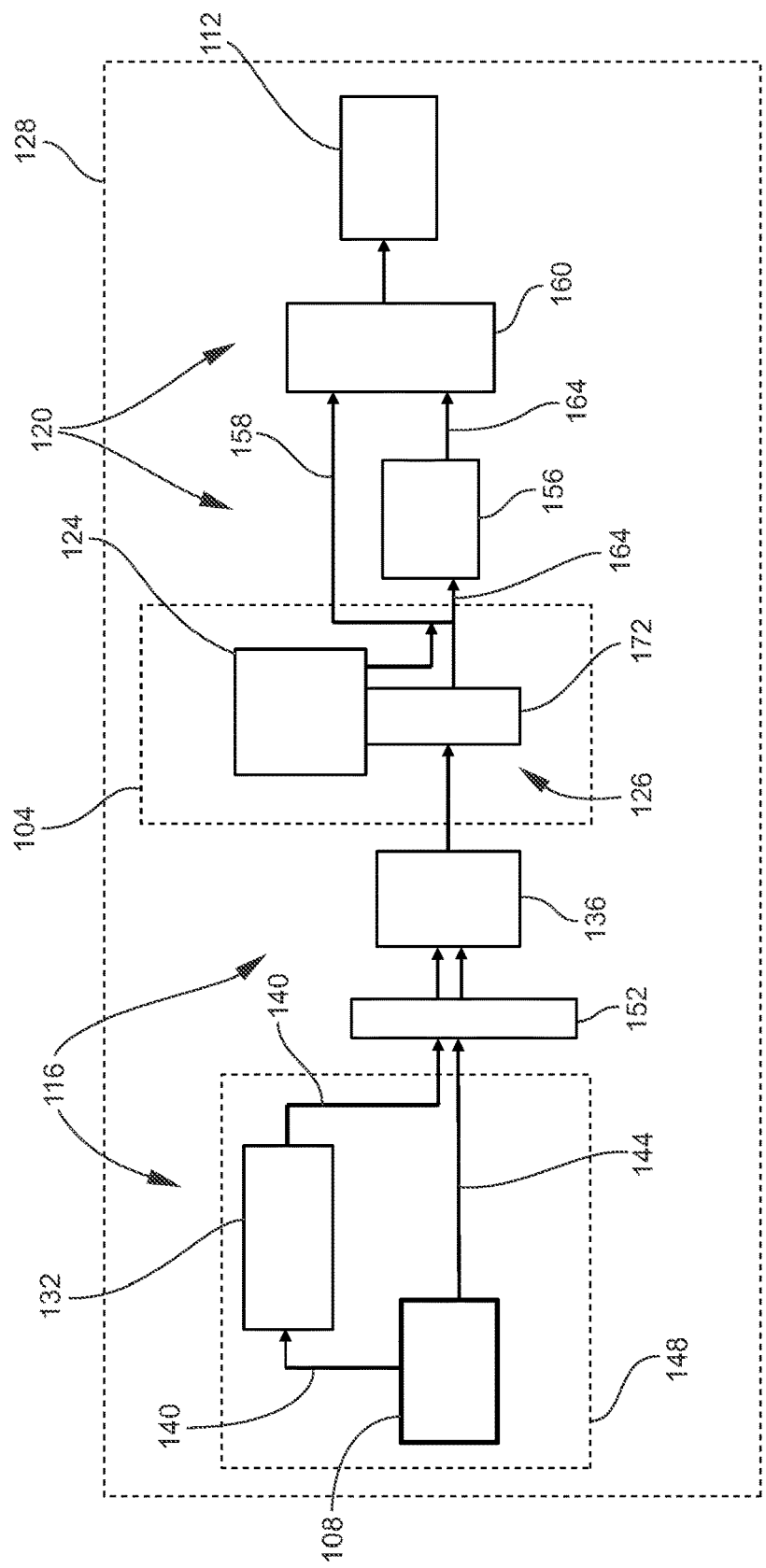
FIG. 1 is a schematic view of an example of a sample analyzing apparatus according to an embodiment.
Figure 2:
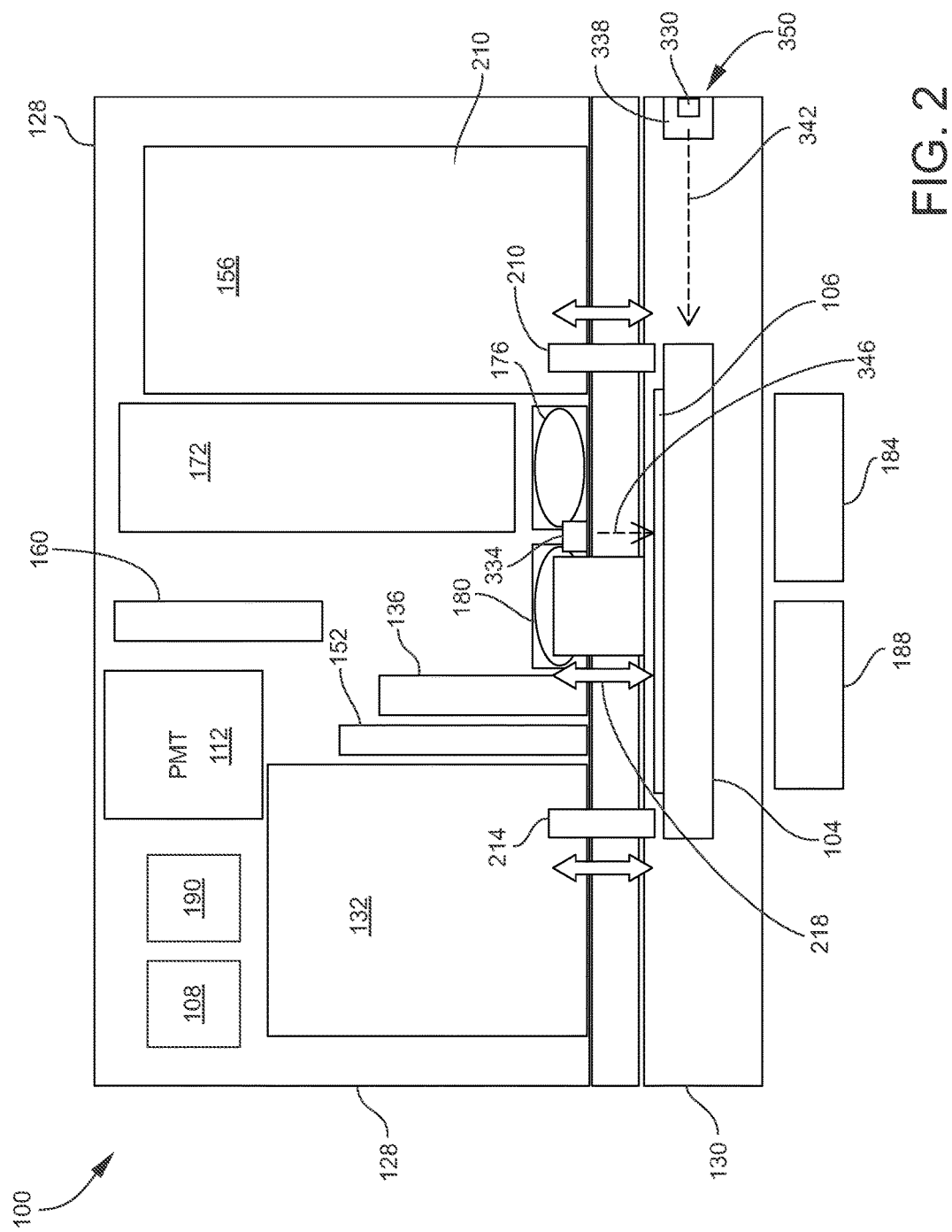
FIG. 2 is another schematic view of the sample analyzing apparatus.

FIG. 1 is a schematic view of an example of a sample analyzing apparatus 100 according to some embodiments. In FIG. 1, the various components of the sample analyzing apparatus 100 are schematically arranged generally in the overall direction of light transmission from one component to another component. FIG. 2 is another schematic view of the sample analyzing apparatus 100. FIG. 2 may generally be taken to be an elevation view, with the understanding that the components generally have been arranged in an arbitrary manner. In actual embodiments, the relative positions of the components to each other may differ significantly from what is schematically depicted or suggested in FIGS. 1 and 2.

The sample analyzing apparatus 100 is configured for performing one or more types of optical-based measurements on a sample (or on multiple samples) to detect or measure analytes of interest. In some embodiments, the sample analyzing apparatus 100 is configured to enable a user to select a desired type of optical measurement to be performed, such as measurements based on fluorescence, absorbance, luminescence, cell imaging, etc. For example, the user may be able to reconfigure the optics of the sample analyzing apparatus 100 to perform a desired type of optical measurement. Thus, in some embodiments the sample analyzing apparatus 100 may be a multi-mode reader. For example, as a multi-mode reader the sample analyzing apparatus 100 may be reconfigurable by enabling a user to select an application-specific cartridge among a number of different cartridges available, and load the selected cartridge into the sample analyzing apparatus 100 so as to establish optical and electrical circuits specific to the desired application. In this manner, the selected cartridge may be operatively coupled to the sample analyzing apparatus 100 whereby the sample analyzing apparatus 100 is properly configured for carrying out the selected experiment. Each cartridge may contain internal optics specific to or optimized for a particular type of experiment (e.g., fluorescence, absorbance, luminescence, etc.). The internal optics housed within the cartridge may communicate with external optics housed within the housing of the sample analyzing apparatus 100 through optical ports of the cartridge's housing. Some cartridges may additionally include one or more internal light sources and/or one or more internal light detectors. The sample analyzing apparatus 100 may be configured to receive and support more than one cartridge at the same time, and a particular cartridge may thereafter be selected for coupling into the optical path defined by the sample analyzing apparatus 100, such as by moving the selected cartridge to an operative position in the interior of the sample analyzing apparatus 100. Examples of cartridge-based multi-mode readers are described in U.S. Pat. Nos. 9,188,527 and 8,119,066, the contents of which are incorporated by reference herein in their entireties.

Generally, the structure and operation of the various components provided in optical-based sample analysis instruments are understood by persons skilled in the art, and thus are only briefly described herein to facilitate an understanding of the presently disclosed subject matter. In the illustrated embodiment, the sample analyzing apparatus 100 includes a sample carrier 104 configured for supporting one or more samples under analysis, a light source 108 for generating excitation light, a light detector 112 for receiving and measuring emission light propagating from the sample (e.g., by fluorescence or luminescence), excitation optics 116 configured for directing the excitation light along an excitation light path from the light source 108 to the sample and processing or modifying the excitation light in one or more ways, and emission optics 120 configured for directing emission light along an emission light path from the sample (e.g., emitted by the sample by fluorescence or luminescence) to the light detector 112 and processing or modifying the excitation light in one or more ways. When configured as a multi-mode reader, the sample analyzing apparatus 100 may further include a cartridge module 124 configured to removably receive and support and plurality of application-specific cartridges configured for implementing specific optics-based measurements (e.g., fluorescence, absorbance, luminescence, etc.) as described above, and intermediate or interface optics 126 configured for providing optical interfaces between a selected cartridge and the excitation optics 116 and emission optics 120. The sample analyzing apparatus 100 further includes an apparatus housing 128 that encloses the sample carrier 104 and cartridge module 124 (when in operative positions for carrying out optical measurements on the sample), as well as other components of the sample analyzing apparatus 100 such as the light source 108, light detector 112, excitation optics 116, and emission optics 120. The apparatus housing 128 may include one or more panels, doors, drawers, etc. for allowing access to interior regions of the sample analyzing apparatus 100, including for loading samples onto the sample carrier 104 and cartridges into the cartridge module 124. The sample analyzing apparatus 100 may further include an incubation chamber 130 (FIG. 2) in the apparatus housing 128, at which the sample(s) (supported on the sample carrier 104) may be operatively located.

Generally, the sample carrier 104 is configured for moving one or more samples along one or more axes. For example, the sample carrier 104 may be an X-Y stage movable in two dimensions in a horizontal plane, although in other embodiments may also be movable in a third vertical (Z) dimension. The sample carrier 104 may be a manually actuated, semi-automated, or fully-automated (motorized) stage or platform. In typical embodiments, one or more samples are supported or held by a suitable sample support 106 (FIG. 2), which is in turn supported by the sample carrier 104. Generally, the sample support 106 may be one or more containers configured for holding one or more samples during an analysis. As non-limiting examples, the sample support 106 may be a multi-well plate (also known as a microtiter plate, microplate, or optical plate), one or more cuvettes or vials, a substrate supporting spots or blots containing respective samples, etc. The sample carrier 104 may be movable into and out from the apparatus housing 128. Thus a sample, or sample support 106 that supports one or more samples, may be mounted onto the sample carrier 104 while the sample carrier 104 is at an outside position, e.g., where the sample carrier 104 is positioned at least partially outside the apparatus housing 128. The sample carrier 104 may then be moved to an inside position at which the sample carrier 104 is positioned entirely in the apparatus housing 128 (as illustrated in FIG. 1) so as to align the sample (or successively align multiple samples) with one or more optical components of the sample analyzing apparatus 100.

The light source 108 is utilized in embodiments requiring excitation (irradiation) of the sample, such as fluorescence and absorbance detection techniques. In some embodiments, the light source 108 is a broadband light source such as a flash lamp (e.g., a xenon flash lamp, deuterium flash lamp, halogen flash lamp, metal halide flash lamp, etc.), which may be configured to produce a pulsed light beam. In other embodiments, other light sources such as light emitting diodes (LEDs), laser diodes (LDs), lasers, etc. may be provided, and the sample analyzing apparatus 100 may be configured to enable switching between different types of light sources, as appreciated by persons skilled in the art.

Generally, the excitation optics 116 may include, for example, one or more lenses, apertures, filters, light guides (e.g., optical fibers), mirrors, beam splitters, monochromators, diffraction gratings, prisms, optical path switches, etc. In the present embodiment, the excitation optics 116 may include an excitation monochromator 132 and/or an excitation filter holder 136. As appreciated by persons skilled in the art, the excitation monochromator 132 and the excitation filter holder 136 both function as wavelength selectors for controlling the specific wavelength (or narrow band of wavelengths) of the excitation light to be passed further through the optical system. That is, the excitation monochromator 132 and the excitation filter holder 136 both function to receive the excitation light from the light source 108 and transmit the excitation light onwards at a desired wavelength or narrow band of wavelengths (colors), but operate on different principles.

The excitation monochromator 132 comprises one or more diffraction gratings that spatially separate the different wavelengths of the excitation light. The excitation monochromator 132 transmits the component of the excitation light having a selected wavelength by rotating the diffraction grating(s) to a position that aligns the excitation light having the selected wavelength with an exit slit. All components of the excitation light having non-selected wavelengths are not aligned with the exit slit, and thus are blocked from propagating in the optical path beyond the excitation monochromator 132.

On the other hand, the excitation filter holder 136 supports a plurality of optical filters composed of materials having different optical transmission characteristics. That is, the optical filters are formulated to pass different wavelengths of the excitation light. The excitation filter holder 136 is configured so as to be movable, either by rotation or (in the illustrated embodiment) linear translation (i.e., sliding). Hence, the excitation filter holder 136 may be actuated so as to move a selected filter into the optical path, whereby the selected filter allows passage of only the selected wavelength (or narrow band of wavelengths) onward in the optical path beyond the excitation filter holder 136, while blocking all other wavelengths. In one embodiment the excitation filter holder 136 comprises eight positions, including up to six positions occupied by optical filters (e.g., long pass, short pass, band pass, etc.), another position being an open aperture through which the excitation light can pass without any interference, and another position presenting a material that blocks the excitation light completely.

In an embodiment including both the excitation monochromator 132 and the excitation filter holder 136, the optical path provided for excitation light to be transmitted from the light source 108 to the excitation filter holder 136 may be split into a first excitation light path 140 and a second excitation light path 144. As schematically illustrated in FIG. 1, the excitation monochromator 132 is in (i.e., optically communicates with, or operates in) the first excitation light path 140 only. Thus, the first excitation light path 140 directs excitation light from the light source 108, through the excitation monochromator 132, through the selected excitation filter of the excitation filter holder 136, and onward to the sample (appropriately positioned at the sample carrier 104). The second excitation light path 144 directs excitation light from the light source 108, through the selected excitation filter of the excitation filter holder 136, and to the sample while bypassing the excitation monochromator 132. In the illustrated embodiment, the sample analyzing apparatus 100 is configured for switching the optical path between the first excitation light path 140 and the second excitation light path 144. In other words, the sample analyzing apparatus 100 is configured for selecting whether the excitation light generated by the light source 108 is directed through the first excitation light path 140 or through the second excitation light path 144, and thereby selects whether or not the excitation monochromator 132 is bypassed. For this purpose, the excitation optics 116 include an excitation path selection device 148. As described further below, the excitation path selection device 148 is movable (can be actuated to move) so as to direct the excitation light from the light source 108 into either the first excitation light path 140 or the second excitation light path 144. As will also become evident, the excitation path selection device 148 may comprise only a single movable component, i.e., only a single movable component is needed to guide the excitation light into the selected (first or second) excitation light path 140 or 144.

As also illustrated in FIG. 1, in some embodiments the excitation optics 116 may further include an additional optics holder 152 that holds a plurality of different optics components. The additional optics holder 152 is movable (by rotation or sliding) so as to insert a selected optics component into the first excitation light path 140 between the excitation monochromator 132 and the excitation filter holder 136, and into the second excitation light path 144 between the light source 108 and the excitation filter holder 136. The additional optics holder 152 may include one or more attenuation filters providing different attenuation factors (e.g., no attenuation, 10D, 20D, 30D, etc.) to reduce the energy of the excitation light in the event that samples with a high response are measured that would saturate the light detector 112. A reference beam splitter (not shown) following the additional optics holder 152 may split off a portion of the excitation light beam as a reference beam that is directed to a reference photodiode (note shown). The reference photodiode may be utilized to track the energy of the excitation light. Based on the intensity of the excitation light measured by the reference photodiode, a system controller (computing device) 190 (FIG. 2) of the sample analyzing apparatus 100 may attenuate the excitation light by actuating the additional optics holder 152 to move so as to insert an attenuation filter of a selected attenuation factor into the active excitation light path 140 or 144. Such technique of dynamic range extension may be implemented as described in U.S. Patent Application Publication No. U.S. 2013/0119277, the entire contents of which are incorporated by reference herein. In addition or as an alternative to attenuation filters, other examples of optics components that may be positioned at the additional optics holder 152 include, but are not limited to, beam-shaping apertures, open apertures (i.e., apertures that do not attenuate or modify the light beam passing therethrough), and filters with specialized functions (e.g., long pass, short pass, band pass, etc.).

Generally, the emission optics 120 may include, for example, one or more lenses, apertures, filters, light guides (e.g., optical fibers), mirrors, beam splitters, monochromators, diffraction gratings, prisms, optical path switches, etc. In the present embodiment, the emission optics 120 may include an emission monochromator 156 and/or an emission filter holder 160. The emission filter holder 160 may support a plurality of emission filters having different light transmission characteristics. The emission monochromator 156 and the emission filter holder 160 may generally be similar to the excitation monochromator 132 and the excitation filter holder 136 described herein, and may be optimized as needed for use in the emission light path.

In an embodiment including both the emission monochromator 156 and the emission filter holder 160, the optical path provided for emission light to be transmitted from the sample (or intervening cartridge and/or interface optics 126, depending on the measurement technique being implemented) to the light detector 112 may be split into a first emission light path 164 and a second emission light path 168. As schematically illustrated in FIG. 1, the emission monochromator 156 is in (i.e., optically communicates with, or operates in) the first emission light path 164 only. Thus, the first emission light path 164 directs emission light through the emission monochromator 156, through the selected emission filter of the emission filter holder 160, and onward to the light detector 112. The second emission light path 168 directs emission light through the selected emission filter of the emission filter holder 160, and to the light detector 112 while bypassing the emission monochromator 156. In the illustrated embodiment, the sample analyzing apparatus 100 is configured for switching the emission light path between the first emission light path 164 and the second emission light path 168. In other words, the sample analyzing apparatus 100 is configured for selecting whether or not the emission monochromator 156 is bypassed. In the present embodiment, the interface optics 126 include a main optical path selection device 172 configured for switching between the first emission light path 164 and the second emission light path 168.

Generally, the light detector 112 is configured to generate electrical measurement signals in response to receiving emission light signals from the emission optics 120, and transmit the measurement signals to signal processing circuitry (e.g., data acquisition circuitry) provided with or external to the sample analyzing apparatus 100 (e.g., as generally represented by a system controller 190, described below). Depending on the embodiment, the light detector 112 may be a photomultiplier tube (PMT), a photodiode, a charge-coupled device (CCD), an active-pixel sensor (APS) such as a complementary metal-oxide-semiconductor (CMOS) device, etc., as needed to optimize sensitivity to the emission wavelengths to be detected. In a typical embodiment, the illustrated light detector 112 comprises one or more PMTs optimized for processing fluorescence and/or luminescence emission light signals. A separate light detector (not shown in FIGS. 1 and 2) optimized for processing absorbance emission light signals, such as a photodiode, may be provided.

As described above, the cartridge module 124 is configured to removably receive and support and plurality of application-specific cartridges configured for implementing specific optics-based measurements (e.g., fluorescence, absorbance, luminescence, cell imaging, etc.). For this purpose, the cartridge module 124 may include a plurality of receptacles or slots into which individual cartridges may be installed (loaded) and thereafter uninstalled (removed). The cartridge module 124 may be movable in an automated, semi-automated, or manual manner. For example, the cartridge module 124 may be movable through a door of the apparatus housing 128 to an at least partially outside position that facilitates installation and uninstallation of cartridges. As another example, the cartridge module 124 may be movable within the interior of the apparatus housing 128 to enable a selected cartridge to be optically aligned with the optical system of the sample analyzing apparatus 100 (i.e., placed in optical communication with the excitation optics 116 and emission optics 120). Depending on the type of experiment for which a given cartridge is utilized, the internal optics enclosed by the cartridge housing of the cartridge may include various components such as, for example, mirrors, filters, prisms, diffraction gratings, internal light sources, and/or internal light detectors.

Generally, the interface optics 126 may include, for example, one or more lenses, optical read heads, apertures, filters, light guides (e.g., optical fibers), mirrors, beam splitters, optical path switches, etc. In the present embodiment, the interface optics 126 include the main optical path selection device 172. In addition to being configured to switch between the first emission light path 164 and the second emission light path 168, the main optical path selection device 172 may be configured to select a measurement method by selecting appropriate optical paths between the excitation optics 116 and the sample, and between the sample and the emission optics 120. The main optical path selection device 172 may also be configured to select whether the cartridge module 124 (i.e., a specific cartridge installed in the cartridge module 124) is placed in optical communication with (is inserted into) the optical path (excitation light path and/or emission light path). For these purposes, the main optical path selection device 172 may include a structural body at which various optical components are mounted, attached, or formed, such as, for example, one or more lenses, apertures, light guides (e.g., optical fibers), mirrors, beam splitters, etc. The structural body of the main optical path selection device 172 may provide a plurality of selectable positions, and may be movable (e.g., slidable) to select which position is to be the operable or active position in the optical path.

As illustrated in FIG. 2, the interface optics 126 may further include a top absorbance lens 176 (a lens utilized for absorbance measurements) positioned above the sample carrier 104 (in alignment with a selected sample supported on the sample carrier 104), a top fluorescence/luminescence lens 180 (a lens utilized for fluorescence and luminescence measurements) positioned above the sample carrier 104 (in alignment with a selected sample supported on the sample carrier 104), a bottom absorbance read head 184 positioned below the sample carrier 104 (in alignment with a selected sample supported on the sample carrier 104), and a bottom fluorescence read head 188 positioned below the sample carrier 104 (in alignment with a selected sample supported on the sample carrier 104). In some embodiments, the top fluorescence/luminescence lens 180 may be movable toward and away from the sample to accommodate different multi-well plate sizes, fill volumes, sample heights, etc., and to avoid cross-talk among neighboring wells of the multi-well plate.

The selection of a measurement method may entail operating the excitation path selection device 148 to select the first excitation light path 140 or the second excitation light path 144 as described herein, in conjunction with operating the main optical path selection device 172 to select a position. The main optical path selection device 172 may also be configured to select whether the emission light is transmitted through the emission monochromator 164 or through the emission filter holder 160. As one non-limiting example, the main optical path selection device 172 may provide the following selectable positions:

One or more positions utilized to couple an application-specific cartridge of the cartridge module 124 into the optical path to provide extended system capabilities, such as time-resolved fluorescence, multiplexed time-resolved fluorescence, fluorescence polarization, ALPHASCREEN® assays, NANO-TRF® assays, etc.

One or more positions utilized for absorbance measurements in conjunction with a selected combination of excitation and/or emission wavelength selectors (e.g., excitation monochromator 132, excitation filter holder 136, emission monochromator 164, and/or emission filter holder 160). The excitation light beam is directed to the top absorbance lens 176. The top absorbance lens 176 is a focusing lens that collimates the excitation light beam such that the focal point of the beam is in the center of the sample. The emission light (in this case, the light transmitted through the sample) is collected by the bottom absorbance read head 184. The transmitted light may then be directed to an absorbance-specific light detector (e.g., a photodiode, not shown in FIG. 1).

One or more positions utilized for luminescence measurements in conjunction with the emission monochromator 164 and/or emission filter holder 160. As appreciated by persons skilled in the art, luminescence measurements do not utilize excitation light, but rather luminescence is initiated by adding an appropriate reagent to the sample. Luminescent emission light from the sample is collected by the top fluorescence/luminescence lens 180, and is directed through the emission optics 120 to the light detector 112.

One or more positions utilized for bottom-read fluorescence measurements in conjunction with a selected combination of excitation and/or emission wavelength selectors (e.g., excitation monochromator 132, excitation filter holder 136, emission monochromator 164, and/or emission filter holder 160). The excitation light is directed via an excitation optical fiber (not shown) to the bottom fluorescence read head 188, which focuses the excitation light beam on the sample (thereby irradiating the sample from the bottom of the multi-well plate). The emission light (in this case, the fluorescence light emitted from the sample) is collected by the bottom fluorescence read head 188. The emission light may then be directed to main optical path selection device 172 via an emission optical fiber (not shown), and then onward through the emission optics 120 to the light detector 112.

One or more positions utilized for top-read fluorescence measurements in conjunction with the excitation monochromator 132 and the emission monochromator 164, or in conjunction with the excitation filter holder 136 and the emission monochromator 164. At this position, the emission light is directed to the top fluorescence/luminescence lens 180, which focuses the excitation light beam on the sample (thereby irradiating the sample from the top of the multi-well plate). The emission light may then be collected by the same top fluorescence/luminescence lens 180, and then onward through the emission optics 120 to the light detector 112.

One or more positions utilized for microscopy (e.g., cell imaging), which may be fluorescence-based microscopy. At this position, optical elements defining light paths utilized for microscopy are coupled into the optical system of the sample analyzing apparatus 100 as needed to illuminate/excite the sample and acquired images from the sample.

Referring to FIG. 2, in some embodiments, the sample analyzing apparatus 100 may further include a liquid injecting system. The liquid injecting system may include one or more injector nozzle(s) (or needle(s)) 210, and associated fluid conduits (tubing), pump(s), reservoir(s), etc. (not shown) configured for adding a liquid to the sample (e.g., into selected wells of the sample support 106 or onto selected blots of the sample support 106 disposed on the sample carrier 104) before or after the sample has been operatively positioned in the sample analyzing apparatus 100. For example, a labeling agent may be added to the sample for fluorescence, luminescence or other types of measurements, as appreciated by persons skilled in the art. In some embodiments, two or more different types of reagents may be added. As depicted by an arrow in FIG. 2, the injector nozzle 210 may be movable in the vertical direction (along the z-axis) toward and away from a sample supported on the sample support 106. For this purpose, the injector nozzle 210 may be mounted to a motorized stage. The motorized stage may also be configured to move the injector nozzle 210 in horizontal directions (along the x-axis and y-axis) to precisely locate the injector nozzle 210 above a selected sample container (e.g., microplate well or blot) of the sample support 106.

In some embodiments, the sample analyzing apparatus 100 may further include a liquid pipetting system. The liquid pipetting system may include one or more pipette tips 214, and associated fluid conduits (tubing), pump(s), reservoir(s), etc. (not shown), configured for transporting liquids (e.g., solutions) to and from the sample carrier 104, particularly to and from a sample support 106 disposed on the sample carrier 104 before or after the sample support 106 has been mounted on the sample carrier 104. The liquid pipetting system is further configured for dispensing precise amounts of liquid into selected wells of the sample support 106 (or onto selected blots of the sample support 106 disposed on the sample carrier 104) and/or aspirating precise amounts of liquid therefrom, which may be done before or after the sample has been operatively positioned in the sample analyzing apparatus 100. As depicted by an arrow in FIG. 2, the pipette tip 214 may be movable in the vertical direction (along the z-axis) toward and away from a sample supported on the sample support 106. For this purpose, the pipette tip 214 may be mounted to a motorized stage (e.g., a pipettor head). The motorized stage may also be configured to move the pipette tip 214 in horizontal directions (along the x-axis and y-axis) to precisely locate the pipette tip 214 above a selected sample container (e.g., microplate well or blot) of the sample support 106.

In some embodiments, the sample analyzing apparatus 100 may further include a microscopy (e.g., cell imaging) system. The microscopy system may include an objective lens 218 (or other type of movable optical lens) and associated optics (e.g., other types of lenses, diaphragms, apertures, mirrors, beam splitters, excitation filters, emission filters, etc., not shown), and also a light source and a light detector. The microscopy system is configured for establishing an excitation path from the light source to a selected sample supported on the sample carrier 104 to illuminate the sample (or to excite fluorophores of the sample in the case of fluorescence microscopy), establishing an emission path from the sample to the light detector to carry emission light emitted from the sample (which may be in response to fluorescent excitation in the case of fluorescence microscopy), and acquiring images from the sample based on the emission light received by the light detector. The light source utilized for the microscopy system may different from the illustrated light source 108 utilized for fluorescence or absorbance measurements. Alternatively, the interface optics 126 (FIG. 1) may be adjustable (e.g., to another position of the main optical path selection device 172) to couple the light beam produced by the light source 108 into the microscopy system. The light detector utilized for the microscopy system may different from the illustrated light detector 112 utilized for fluorescence measurements. The light detector utilized for the microscopy system is typically a multi-pixel light detector such as a camera. Additionally or alternatively, a microscopy-specific cartridge loaded into the cartridge module 124 (FIG. 1, if provided) containing some or all of the components of the microscopy system may be utilized.

As depicted by an arrow in FIG. 2, the objective lens 218 may be movable in the vertical direction (along the z-axis) toward and away from a sample supported on the sample support 106, for focusing images and scanning the sample through its thickness along the z-axis. For this purpose, the objective lens 218 may be mounted to a motorized stage. The motorized stage may also be configured to move the objective lens 218 in horizontal directions (along the x-axis and y-axis) to precisely locate the objective lens 218 above a selected sample container (e.g., microplate well or blot) of the sample support 106.

Referring to FIG. 2, the sample analyzing apparatus 100 may further include a system controller (e.g., a computing device) 190. As appreciated by persons skilled in the art, the system controller 190 may include one or more modules configured for controlling, monitoring and/or timing various functional aspects of the sample analyzing apparatus 100, and/or for receiving data or other signals from the sample analyzing apparatus 100 such as measurement signals from the light detector 112 and transmitting control signals to the light detector 112 and/or other components. For example, the system controller 190 may be configured for coordinating the operations (e.g., movements and positions) of the sample carrier 104, the cartridge module 124 (if provided), the excitation monochromator 132, the excitation filter holder 136, the excitation path selection device 148, the emission monochromator 156, the emission filter holder 160, the main optical path selection device 172, the injector nozzle 210, the pipette tip 214, and the objective lens 218. For all such purposes, the system controller 190 may communicate with various components of the sample analyzing apparatus 100 via wired or wireless communication links. In typical embodiments, the system controller 190 includes a main electronic processor providing overall control, and may include one or more electronic processors configured for dedicated control operations or specific signal processing tasks. The system controller 190 may also include one or more memories and/or databases for storing data and/or software. The system controller 190 may also include a computer-readable medium that includes instructions for performing any of the methods disclosed herein. The functional modules of the system controller 190 may comprise circuitry or other types of hardware (or firmware), software, or both. For example, the modules may include signal processing (or data acquisition) circuitry for receiving measurement signals from the light detector 112 and software for processing the measurement signals such as for generating graphical data. The system controller 190 may also include or communicate with one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 190 may include an operating system (e.g., Microsoft Windows® software) for controlling and managing various functions of the system controller 190.

Figure 3:
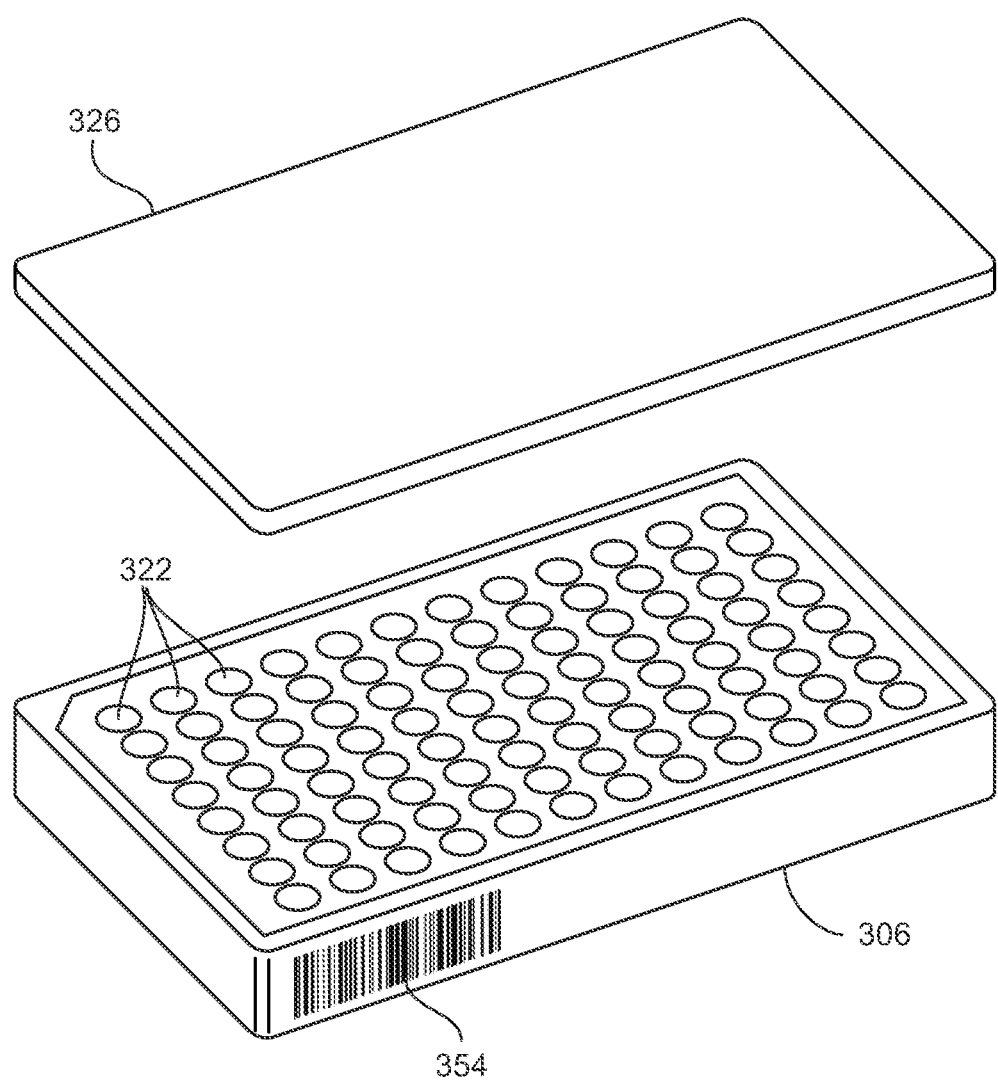
FIG. 3 is a perspective view of an example of a microplate and a plate lid that may be utilized in a sample analyzing apparatus such as illustrated in FIGS. 1 and 2, according to an embodiment.

FIG. 3 is a perspective view of a microplate 306 that may be utilized in the sample analyzing apparatus 100 illustrated in FIGS. 1 and 2. The microplate 306 may correspond to the sample support 106 illustrated in FIG. 2, and thus may be mounted on the sample carrier 104. The microplate 306 includes a two-dimensional array of wells 322 utilized to contain respective samples to be analyzed. In a typical embodiment, the two-dimensional array is a 2:3 rectangular matrix. Typical examples include 96, 384 or 1536 wells 322, although the total number of wells 322 may be less than 96 or more than 1536. The wells 322 may be polygonal (as illustrated) or cylindrical. Depending on the analysis to be performed, the wells 322 may contain various solutions and reagents. The wells 322 are individually addressable by various optical-related components (e.g., the top absorbance lens 176, top fluorescence/luminescence lens 180, bottom absorbance read head 184, bottom fluorescence read head 188, and objective lens 218) and fluidic components (e.g., the injector nozzle 210 and pipette tip 214) described herein. For optical reading from the bottom of the microplate 306, the wells 322 are optically transparent. Depending on the analysis to be performed, a plate lid 326 may be mounted to the top of the microplate 306 to cover the wells 322. The lid 326 may be opaque to block light from propagating into or out from the top of the microplate 306. The lid 326 may be utilized, for example, in conjunction with optical reading from the bottom of the microplate 306.

As also illustrated in FIG. 3, the microplate 306 may include one or more barcode labels 354 on which barcode (e.g., one-dimensional (1D) barcode, two-dimensional (2D) barcode such as QR barcode) is printed. The barcode labels 354 may be provided on one or more sides of the microplate 306. The barcodes may contain various types of information such as, for example, the identity of the microplate 306 and/or samples contained in the microplate 306. The barcodes may be read by an appropriate reading device, as appreciated by persons skilled in the art.

According to some embodiments, an experiment entailing optical measurement utilizing the sample analyzing apparatus 100 may be implemented as follows. The sample or samples are introduced into the sample analyzing apparatus 100 and placed in a proper operating position relative to optics and other components of the sample analyzing apparatus 100. Generally, the "operating" position of the sample is an "optically aligned" position, i.e., a position that establishes an optical path sufficient for optical data acquisition from the sample. Depending on the experiment, the operating position may also correspond to the sample being "fluidly aligned" with the sample analyzing apparatus 100, i.e., positioned so as to be able to dispense fluid onto the sample such as by operating a liquid injecting system as described above, and/or operating a liquid pipetting system to dispense fluid into and/or aspirate fluid from sample containers or blots of the sample support 106. Sample introduction may entail loading one or more samples in one or more wells of a microplate or other type of sample support 106 (e.g., preparing samples in accordance with blotting techniques such as Western Blot, as appreciated by persons skilled in the art), and loading or mounting the sample support 106 in the sample analyzing apparatus 100, such as with the use of the sample carrier 104 described above. Depending on the sample and the type of measurement to be made, the sample may be subjected to preparation or treatment (incubation, mixing, homogenization, centrifuging, buffering, reagent addition, analytical separation such as solid phase extraction, chromatography, electrophoresis, etc.) prior to being positioned in the sample analyzing apparatus 100, as appreciated by persons skilled in the art.

In addition to sample introduction, the sample analyzing apparatus 100 or certain components thereof (optics, electronics, etc.) may need to be configured for implementing the specific type of measurement to be made. For example, if cartridge-based, the appropriate cartridge (or cartridges) may be installed in the cartridge module 124 of the sample analyzing apparatus 100. After installing a cartridge, optics provided in the cartridge become part of the optical circuit within the apparatus housing 128 of the sample analyzing apparatus 100. For example, the cartridge optics may be aligned with (in optical communication with) the excitation optics 116, emission optics 120, and/or interface optics 126. Installing the cartridge results in establishing electrical paths for transmitting power, data and control signals to and/or from the cartridge.

The sample is then processed as necessary to induce the emission of photons from the sample for measurement. In the case of luminescence measurement, reagents may be added to induce a luminescent response, such as by operating a liquid injecting system as described above. In the case of fluorescence measurement, the light source 108 and associated excitation optics 116 (and possibly a cartridge and/or the interface optics 126, as described above) are utilized to irradiate or excite the sample to induce a fluorescent response. Fluorescence measurement may additionally entail the addition of reagents to induce the fluorescent response. In the case of either luminescence or fluorescence measurement, the emission optics 120 (and possibly a cartridge and/or the interface optics 126, as described above) are utilized to collect the emission light from the sample and direct the emission light to the light detector 112. The light detector 112 converts these optical signals into electrical signals (detector signals, or measurement signals) and transmits the electrical signals to signal processing circuitry, such as may be provided by a system controller 190 of the sample analyzing apparatus 100 as described above.

In the case of absorbance measurement, the light source 108 and associated excitation optics 116 (and possibly a cartridge and/or the interface optics 126, as described above) are utilized to irradiate the sample. In this case, the "emission" light is the light transmitted through the sample, which is attenuated in comparison to the excitation light incident on the sample due to absorbance by the sample of some of the light. The transmitted ("emission") light may be directed to an absorbance detector that may be separate from the illustrated light detector 112, as described above.

Depending on the embodiment, the method may include operation and/or use of other components of the sample analyzing apparatus 100, such as one or more cartridges of the cartridge module 124, the interface optics 126, the excitation path selection device 148, the excitation monochromator 132, the excitation filter holder 136, the main optical path selection device 172, the emission monochromator 164, the emission filter holder 160, etc., all as described elsewhere herein.

For any of the optical measurement techniques implemented, multiple samples may be processed. For example, the sample support 106 on or in which the multiple samples are provided may be moved (such as by using the sample carrier 104) to sequentially align each sample with the optics being utilized for the experiment, whereby measurements are taken from all samples sequentially.

Referring to FIG. 2, in some embodiments, the sample analyzing apparatus 100 may further include an optical-based monitoring system 350 configured to monitor one or more operating conditions (or states) present in the interior enclosed by the apparatus housing 128 of the sample analyzing apparatus 100. The monitoring system 350 includes one or more light sources and one or more light detectors. The light source(s) are positioned to illuminate region(s) or surface(s) in the interior of the sample analyzing apparatus 100 at which monitoring is desired by the light detector(s). Depending on the particular operating condition or state being monitored, a given light detector may be configured to make an optical-based measurement or to acquire images viewable by a user in real time. The light sources utilized in the monitoring system 350 are typically LEDs, but more generally may be any appropriate type of light sources, such as the other examples noted herein. The light detectors utilized in the monitoring system 350 are typically cameras to enable the capturing of images (still images, or both still images and video). However, for monitoring functions involving detection or measurement not requiring multi-pixel imaging, another type of light detector may be utilized, such as the other examples noted herein.

In the illustrated embodiment, the sample analyzing apparatus 100 includes two light sources 330 and 334 and a camera 338 utilized for monitoring. In other embodiments, more than two light sources 330 and 334 and more than one may camera 338 be included. The light sources 330 and 334 may be positioned and oriented to emit respective light beams 342 and 346 in different directions or angles relative to each other. In the illustrated embodiment, the light beam 342 is oriented horizontally and the light beam 346 is oriented vertically, but more generally the light beams 342 and 346 may be oriented at any angles useful for carrying out the monitoring functions. The camera 338 may be positioned and oriented to receive light reflected or emitted from surfaces or regions illuminated by the light sources 330 and/or 334, and thereby make optical-based measurements to enable a user to view the illuminated surfaces or regions, such as on a display screen communicating with the system controller 190.

FIG. 4 is a perspective view of the monitoring system 350. FIG. 4 illustrates an example of the positions of the light sources 330 and 334 and the camera 338, relative to each other and to other interior components such as the sample carrier 104 and the objective lens 218. The light sources 330 and 334 and the camera 338 may be mounted to appropriate inside surfaces in the housing 128 of the sample analyzing apparatus 100. The light sources 330 and 334 and the camera 338 may communicate with the system controller 190 (FIG. 2) as needed for implementing the monitoring functions of the monitoring system 350. For example, the system controller 190 may transmit control signals to the light sources 330 and 334 and the camera 338, and the camera 338 may transmit output signals (measurement signals) to the system controller 190 for signal processing as needed for optical-based measurement or imaging. The light sources 330 and 334 and the camera 338 may be mounted to appropriate inside surfaces in the housing 128 of the sample analyzing apparatus 100. The light sources 330 and 334 and the camera 338 may be mounted to respective printed circuit boards (PCBs) containing electronics. In some embodiments, such PCBs may be considered as being part of the system controller 190.

Depending the monitoring function(s) to be implemented, the monitoring system 350 may operate before, during, or after a sample analysis as described herein is performed, and may operate in one or more iterations during such time periods to perform one or more different monitoring functions. Notably, the illumination and detecting/imaging functions implemented by the monitoring system 350 are completely internal, i.e., inside the apparatus housing 128. Thus, the operation of the monitoring system 350 does not require opening the apparatus housing 128 and exposing sensitive optical components (e.g., the light detector 112) to the ambient. Examples of monitoring functions, and operating conditions that may be monitored by the monitoring system 350, include, but are not limited to, the following.

Plate presence detection: In an embodiment, the monitoring system 350 is configured to detect the presence of the microplate 306 (or other type of sample support) on the sample carrier 104. If the monitoring system 350 determines that the microplate 306 is not present, the monitoring system 350 may prevent the sample analyzing apparatus 100 (or certain components of the sample analyzing apparatus 100 that would be affected by the absence of the microplate 306) from operating. The monitoring system 350 may take other actions such as, for example, outputting an audio and/or visual indication that informs the user of the absence of the microplate 306. For these functions, the camera 338 may communicate with the system controller 190, as described above. In one embodiment, the light source 334 (FIGS. 3 and 4) is utilized. The light source 334 is positioned above the region of the sample carrier 104 where the microplate 306 is intended to be mounted. The light source 334 is activated to emit the light beam 346 toward this region. The light beam 346 may be oriented vertically or an angle to the vertical. The camera 338 (or another camera located in a different position in the apparatus housing 128, not shown in FIG. 3) is activated to detect light reflected from a surface of the microplate 306. If the camera 338 detects reflected light, the monitoring system 350 determines that the microplate 306 is present. If, on the other hand, the camera 338 does not detect reflected light (i.e., detects the absence of a reflection signal), the monitoring system 350 determines that the microplate 306 is not present, and may initiate further actions as described above.

Additionally, the camera 338 may provide images of the region illuminated by the light source 334. A user may view these images on a display screen, in real time or not, and make a manual determination as to whether the microplate 306 is present or absent.

Additionally or alternatively, the monitoring system 350 may be configured to detect the presence of the microplate 306 by detecting (measuring) the height of the microplate 306. In the present context, the "height" of the microplate 306 is the position of a part of the microplate 306 (typically the top surface or top edge of the microplate 306) along the vertical axis. The height as a value may be calculated relative to any reference datum, such as a point in the apparatus housing 128. If the height detected is lower than a minimum threshold value, the monitoring system 350 may determine that the microplate 306 is not present, and may initiate further actions as described above. For example, if the microplate 306 is not present, then the height measured may be the height of the sample carrier 104 (e.g., the top surface thereof, or a surface on which the microplate 306 is supported when present), which will be lower than the minimum threshold value. A reference point on the surface of the sample carrier 104 may be defined as corresponding to a plate height of zero. The sample carrier 104 may be configured as needed to provide a line of sight between the zero reference point and the light source 334, and a line of sight between the zero reference point and the camera 338.

Monitoring for the presence of the microplate 306 is useful, for example, in a situation where the user forgets to mount the microplate 306 on the sample carrier 104 before initiating sample measurement/analysis operations. This monitoring function is especially important when an injector nozzle 210 or a pipette tip 214 is in use. The injector nozzle 210 or pipette tip 214 could dispense liquid directly onto optical components of the sample analyzing apparatus 100 and damage such optical components.

Plate height detection: In an embodiment, the monitoring system 350 is configured to measure the height of the microplate 306 to determine that the height is correct according to a predetermined height specified for the operation of the sample analyzing apparatus 100. In one embodiment, the light source 334 (FIGS. 3 and 4) is utilized. The light source 334 is positioned to emit the light beam 346 toward the top edge of the microplate 306, thereby creating a light pattern or profile detectable by the camera 338. The detected light pattern may be utilized to calculate the height of the microplate 306. For example, the system controller 190 may process output signals received from the camera 338, and execute an appropriate algorithm, to calculate the height of the microplate 306. The monitoring system 350 may also be configured to measure the distance between the upper surface of the microplate 306 and components operating proximate to the upper surface of the microplate 306 such as, for example, the injector nozzle 210, the pipette tip 214, and the objective lens 218. If the height detected, or the distance between the microplate 306 and another component, is lower than a minimum, the monitoring system 350 may prevent the sample analyzing apparatus 100 (or certain components of the sample analyzing apparatus 100 that would be affected by this operating condition) from operating. This monitoring function of the monitoring system 350 is useful, for example, to avoid collisions between the microplate 306 and the injector nozzle 210, the pipette tip 214, the objective lens 218, or other component, thereby preventing damage to such components.

Plate lid presence detection: In an embodiment, the monitoring system 350 is configured to detect the presence of a plate lid 326 (FIGS. 3 and 4) on the microplate 306. If the use of the plate lid 326 is not prescribed for a particular sample analysis procedure, and the monitoring system 350 detects the presence of the plate lid 326, the monitoring system 350 may prevent the sample analyzing apparatus 100 (or certain components of the sample analyzing apparatus 100 that would be affected by this operating condition) from operating and/or initiate other appropriate actions. This monitoring function is useful, for example, in a situation where the user forgets to remove the plate lid 326 before starting the prescribed measurement on the sample. This monitoring function is especially important when an injector nozzle 210 or a pipette tip 214 is in use. The injector nozzle 210 or pipette tip 214 could dispense liquid onto the plate lid 326, and the liquid could then flow into contact with optical components of the sample analyzing apparatus 100 and damage such optical components. Similarly, if the use of the plate lid 326 is prescribed for a particular sample analysis procedure, and the monitoring system 350 determines that the plate lid 326 is not present, the monitoring system 350 may initiate appropriate actions in response to such operating condition.

Barcode reading: In an embodiment, the monitoring system 350 is configured to operate as barcode reading device to read one or more barcodes printed on one or more barcode labels 354 (FIG. 3) positioned on one or more sides of the microplate 306 mounted on the sample carrier 104. The sample carrier 104 is configured such that when the microplate 306 is mounted on the sample carrier 104, a given barcode label 354 can be adequately illuminated by the light source and light reflected from the barcode label 354 can be fully and accurately captured by the camera so that the barcode can be properly read. For example, the microplate 306 may be sufficiently elevated above the top surface of the sample carrier 104 that large portions of the sides of the microplate 306 potentially containing barcode labels 354 are in the lines of sight of the light source(s) and the camera(s) utilized for barcode reading. As another example, the body of the sample carrier 104 may be structured with features (e.g., recesses, openings, etc.) providing or improving lines of sight with the light source(s) and the camera(s). The light source and the camera may be positioned relative to each other such that the light beam incident on the barcode label 354 and the light beam reflected from the barcode label 354 are not coincident. In one embodiment, the light source 330 and the camera 338 (FIGS. 3 and 4) may be utilized for barcode reading. Additionally, a given microplate 306 may have barcode labels 354 on two or more sides of the microplate 306. If it is desired to read such additional barcode labels 354, the monitoring system 350 may include additional light sources and cameras as needed.

Injector monitoring: In an embodiment, the monitoring system 350 is configured to monitor the operation of the liquid injecting system, particularly the injector nozzle(s) 210 (FIG. 2) during rinsing and priming operations of the liquid injecting system. As appreciated by persons skilled in the art, the fluidic circuitry of the liquid injecting system, including the injector nozzle 210 and associated tubing, are typically rinsed and primed in preparation for an injection operation, such as the injection of reagents or other liquids onto a sample or into a sample container such as the well of a microplate 306. It is desirable to avoid the formation of liquid droplets and liquid-air bubbles on the injector nozzle 210 and nearby tubing. Liquid droplets and bubbles may contaminate one or more wells of the microplate 306, and may spill onto the microplate 306 and flow into contact with optical components of the sample analyzing apparatus 100 and damage such optical components. Liquid droplets and bubbles also may impair the ability of the liquid injecting system to precisely inject predetermined quantities of liquid. One or more light sources 330 and 334 and cameras 338 (FIGS. 3 and 4) of the monitoring system 350 may be utilized to monitor the injector nozzle 210 and nearby tubing for the presence of liquid droplets and air bubbles. In one embodiment, images of the injector nozzle 210 and its surrounding region are acquired by the camera(s) 338 and displayed on a display screen, thereby allowing the user to monitor the injector nozzle 210 and nearby tubing. If the user determines that liquid droplets and/or bubbles are present, the user may shut down further operation of the sample analyzing apparatus 100 so that appropriate efforts can be made to address the problem.

Pipettor monitoring: In an embodiment, the monitoring system 350 is configured to monitor the operation of the liquid pipetting system, particularly the pipette tip(s) 214 (FIG. 2). Pipette tips 214 are typically removable from the pipettor head of the liquid pipetting system so that they can be replaced. During movement and/or use of the pipette tip 214 in the apparatus housing 128, it is possible for the pipette tip 214 to become unsecured and fall from the pipettor head onto the microplate 306 or other components of the sample analyzing apparatus 100, thereby contaminating or damaging such components and/or creating an obstruction into which other moving components may collide. One or more light sources 330 and 334 and cameras 338 (FIGS. 3 and 4) of the monitoring system 350 may be utilized to monitor the pipette tip 214 and ensure it is securely coupled to the pipettor head, and to detect the event of the pipette tip 214 becoming separated from the pipettor head. In one embodiment, images of the pipette tip 214 and its surrounding region are acquired by the camera(s) 338 and displayed on a display screen, thereby allowing the user to monitor the pipette tip 214. If the user determines that pipette tip 214 is not securely coupled or has fallen away from the pipettor head, the user may shut down further operation of the sample analyzing apparatus 100 so that appropriate efforts can be made to address the problem.

Microplate monitoring for liquid droplets: In an embodiment, the monitoring system 350 is configured to monitor the microplate 306. In particular, the monitoring system 350 may be utilized to monitor for the presence of liquid droplets on one or more surfaces of the microplate 306. Such liquid droplets, which may have resulted from operation of the injector nozzle 210 or the pipette tip 214, may contaminate the samples or optical components of the sample analyzing apparatus 100. One or more light sources 330 and 334 and cameras 338 (FIGS. 3 and 4) of the monitoring system 350 may be utilized to monitor the microplate 306 for the presence of liquid droplets. In one embodiment, images of the microplate 306 are acquired by the camera(s) 338 and displayed on a display screen, thereby allowing the user to monitor the microplate 306. If the user determines that liquid droplets are present on the microplate 306, the user may shut down further operation of the sample analyzing apparatus 100 so that appropriate efforts can be made to address the problem.

Microplate monitoring for debugging: In an embodiment, the monitoring system 350 is configured to monitor the respective positions and motions of movable components disposed in the apparatus housing 128 to assist a user in evaluating the operation of the movable components and debugging any errors found in their positions and motions. As described herein, the sample analyzing apparatus 100 includes various fluidic components, optical components, and mechanical components that are movable in the apparatus housing 128 toward and away from the microplate 306. These components include, for example, the injector nozzle 210, the pipette tip 214, the objective lens 218, and the sample carrier 104 on which the microplate 306 is mounted. Typically for a given sample analysis, the positions and respective paths of travel along which these components move (and the timing of such movements) are carefully predetermined by programming, as may be executed and controlled by the system controller 190 (FIG. 2), so that collisions between fluidic/optical/mechanical components, and between fluidic/optical/mechanical components and the microplate 306, are avoided. Due to mechanical malfunctions (e.g., in a drive mechanism, a mechanical coupling, etc.), electronics malfunctions (e.g., in an electrical signal path), and/or programming errors (e.g., in software instructions), it is possible for a component to deviate from its intended travel path or from the intended time during which it is move, thereby risking collision with another component. One or more light sources 330 and 334 and cameras 338 (FIGS. 3 and 4) of the monitoring system 350 may be utilized to monitor one or more such components, determining whether an error in position or motion exists (or has occurred), debug the error (e.g., repair or replace such components or electronics controlling such components, fix errors in programming, etc.), and subsequently verify that such components are operating as prescribed. In one embodiment, images of such components are acquired by the camera(s) 338 and displayed on a display screen, thereby allowing the user to monitor the components. As part of this aspect of monitoring, the light sources 330 and 334 and cameras 338 may be utilized to determine the positions of the components being monitored such as, for example, the heights (positions) of the injector nozzle 210, the pipette tip 214, the objective lens 218, and the microplate 306, as described above.

In other embodiments, the monitoring system 350 is configured to perform any combination of two or more of the foregoing monitoring functions. By providing one or a few light sources 330 and 334 and cameras 338, the monitoring system 350 is able to perform a combination of different monitoring functions, thereby avoiding the increased cost, complexity, and space requirement that would be associated with providing dedicated devices to perform such monitoring functions individually.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller (computing device) 190 schematically depicted in FIG. 2. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), application specific integrated circuits (ASICs), or field-programmable gate arrays (FPGAs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 190 shown in FIG. 2), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample analyzing apparatus for performing an optical-based measurement on a sample, the sample analyzing apparatus comprising:
   a housing;
   a first light source disposed in the housing and configured for generating excitation light;
   excitation optics disposed in the housing and configured for directing the excitation light from the first light source to the sample disposed in multi-well microplate, wherein the sample emits emission light in response to being irradiated by the excitation light;
   a first light detector disposed in the housing and configured for measuring the emission light emitted by the sample in response to being irradiated by the excitation light;
   emission optics disposed in the housing and configured for directing the emission light from the sample to the first light detector;
   one or more liquid handling components configured to deliver liquid to the sample disposed in the multi-well microplate; and
   a monitoring system configured for monitoring an area of the housing in which one or more movable components are located, the area corresponding to a space in which the one or more liquid handling components are configured to periodically interact with the sample disposed in the multi-well microplate, the monitoring system comprising:
      a second light source disposed in the housing and configured for illuminating the one or more movable components; and
      a second light detector disposed in the housing and configured for detecting light reflected from the one or more movable components in response to being illuminated.

2. The sample analyzing apparatus of claim 1, wherein the monitoring system is configured for detecting an operating condition of the one or more movable components.

3. The sample analyzing apparatus of claim 2, wherein the operating condition is selected from the group consisting of:
   the presence of the one or more movable components in the housing;
   a position of the one or more movable components in the housing;
   a distance between a first movable component of the one or more movable components and a second movable component of the one or more movable components disposed in the housing;
   the presence of liquid droplets or bubbles on the one or more movable components;
   a path along which the one or more movable components is moving in the housing; and
   a combination of two or more of the foregoing.

4. The sample analyzing apparatus of claim 2, wherein the monitoring system is configured for shutting down an operation of the sample analyzing apparatus, in response to detecting the operating condition.

5. The sample analyzing apparatus of claim 1, wherein the monitoring system is configured for reading a barcode on a barcode label disposed in the housing.

6. The sample analyzing apparatus of claim 5, wherein the barcode label is disposed on a sample support disposed in the housing.

7. The sample analyzing apparatus of claim 1, wherein the one or more movable components comprises a sample support configured for supporting the sample, and the monitoring system is configured for detecting the presence of the sample support in the housing.

8. The sample analyzing apparatus of claim 1, wherein the one or more movable components comprises a sample support configured for supporting the sample, and the monitoring system is configured for measuring a position of the sample support relative to a reference point in the housing.

9. The sample analyzing apparatus of claim 1, wherein the one or more movable components comprises a sample support configured for supporting the sample, and the monitoring system is configured for detecting the presence of lid mounted on a top surface of the sample support.

10. The sample analyzing apparatus of claim 1, wherein the one or more movable components comprises a sample support configured for supporting the sample, the sample analyzing apparatus further comprises an additional component disposed in the housing, and the monitoring system is configured for measuring a distance between the sample support and the additional component.

11. The sample analyzing apparatus of claim 10, wherein the additional component is selected from the group consisting of: an injector nozzle; a pipette tip; and an optical lens.

12. The sample analyzing apparatus of claim 1, wherein the one or more movable components comprises a sample support configured for supporting the sample, and the monitoring system is configured for detecting the presence of liquid droplets on the sample support.

13. The sample analyzing apparatus of claim 1, wherein the one or more movable components comprises a fluidic component configured for dispensing liquid to the sample, and the monitoring system is configured for measuring a position of the fluidic component relative to a reference point in the housing.

14. The sample analyzing apparatus of claim 13, wherein the fluidic component is selected from the group consisting of: an injector nozzle; and a pipette tip.

15. The sample analyzing apparatus of claim 1, wherein the one or more movable components comprises the one or more liquid handling components, and the monitoring system is configured for detecting the presence of liquid droplets or bubbles on the one or more liquid handling components.

16. The sample analyzing apparatus of claim 1, wherein the one or more movable components is a pipette tip associated with the one or more liquid handling components, the pipette tip configured for being coupled to and movable by the one or more liquid handling components, and the monitoring system is configured for detecting whether the pipette tip has been decoupled from the one or more liquid handling components.

17. The sample analyzing apparatus of claim 1, wherein the second light detector is a camera configured for acquiring images of the movable component.

18. The sample analyzing apparatus of claim 17, comprising a system controller communicating with the camera, and configured for controlling presentation of images acquired by the camera on a display screen external to the housing and viewable by a user.

19. The sample analyzing apparatus of claim 17, comprising a system controller communicating with the camera, and configured for controlling playback of video images acquired by the camera on a display screen external to the housing and viewable by a user.

20. A method for monitoring a movable component of a sample analyzing apparatus, the sample analyzing apparatus comprising a housing in which the movable component is disposed, a first light source disposed in the housing and configured for generating excitation light, excitation optics disposed in the housing and configured for directing the excitation light from the first light source to a sample disposed in multi-well microplate, a first light detector disposed in the housing and configured for measuring emission light emitted from the sample in response to being irradiated by the excitation light, and emission optics disposed in the housing and configured for directing the emission light from the sample to the first light detector, one or more liquid handling components configured to deliver liquid to the sample disposed in the multi-well microplate the method comprising:

operating a monitoring system to monitor the movable component by:
operating a second light source disposed in the housing to illuminate the movable component; and
operating a second light detector disposed in the housing detect light reflected from the movable component in response to being illuminated.

21. The method of claim 20, wherein operating the monitoring system comprises performing an operation selected from the group consisting of:
operating the second light source and the second light detector to detect the presence of the movable component in the housing;
operating the second light source and the second light detector to detect a position of the movable component in the housing;
operating the second light source and the second light detector to calculate a distance between the movable component and an additional component disposed in the housing;
operating the second light source and the second light detector to detect the presence of liquid droplets or bubbles on the movable component;
operating the second light source and the second light detector to monitor a path along which the movable component is moving in the housing;
operating the second light source and the second light detector to read a barcode on a barcode label disposed in the housing; and
a combination of two or more of the foregoing.

* * * * *